(12) United States Patent
Munblit et al.

(10) Patent No.: US 11,033,549 B2
(45) Date of Patent: *Jun. 15, 2021

(54) USE OF HETEROCYCLIC COMPOUNDS IN THE TREATMENT OF PIGMENTED SKIN

(71) Applicant: ATIR Holding S.A., Luxembourg (LU)

(72) Inventors: Izabella Munblit, Jerusalem (IL); Karina Tsipe, Modiln (IL)

(73) Assignee: ATIR Holding S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 16/493,317

(22) PCT Filed: Mar. 14, 2018

(86) PCT No.: PCT/IB2018/051703
§ 371 (c)(1),
(2) Date: Sep. 12, 2019

(87) PCT Pub. No.: WO2018/167687
PCT Pub. Date: Sep. 20, 2018

(65) Prior Publication Data
US 2020/0085826 A1     Mar. 19, 2020

Related U.S. Application Data

(60) Provisional application No. 62/470,898, filed on Mar. 14, 2017.

(51) Int. Cl.
*A61K 31/517*   (2006.01)
*A61P 17/00*    (2006.01)
*A61K 8/49*     (2006.01)
*A61K 9/00*     (2006.01)
*A61Q 19/02*    (2006.01)

(52) U.S. Cl.
CPC .......... *A61K 31/517* (2013.01); *A61K 8/4953* (2013.01); *A61K 9/0014* (2013.01); *A61P 17/00* (2018.01); *A61Q 19/02* (2013.01)

(58) Field of Classification Search
CPC ..... A61K 31/498; A61K 31/517; A61P 17/00; C07D 239/90; C07D 403/06
USPC ...................... 514/252.17; 544/286
See application file for complete search history.

(56) References Cited

U.S. PATENT DOCUMENTS

| 2015/0111897 A1 | 4/2015 | Hu et al. |
| 2020/0069549 A1 | 3/2020 | Lurya et al. |

FOREIGN PATENT DOCUMENTS

| WO | WO 03/063875    | 8/2003  |
| WO | WO 2004/037183  | 5/2004  |
| WO | WO 2007/110868  | 10/2007 |
| WO | WO 2008/117269  | 10/2008 |
| WO | WO 2010/019450  | 2/2010  |
| WO | WO 2011/075655  | 6/2011  |
| WO | WO 2012/140642  | 10/2012 |
| WO | WO 2018/167687  | 9/2018  |
| WO | WO 2018/167689  | 9/2018  |

OTHER PUBLICATIONS

International Preliminary Report on Patentability dated Sep. 26, 2019 From the International Bureau of WIPO Re. Application No. PCT/IB2018/051703. (7 Pages).
International Preliminary Report on Patentability dated Sep. 26, 2019 From the International Bureau of WIPO Re. Application No. PCT/IB2018/051706. (6 Pages).
Requisition by the Examiner dated Nov. 15, 2019 From the Innovation, Science and Economic Development Canada, Canadian Intellectual Property Office Re. Application No. 3,055,881. (4 Pages).
Requisition by the Examiner dated May 13, 2020 From the Innovation, Science and Economic Development Canada, Canadian Intellectual Property Office Re. Application No. 3,055,881. (5 Pages).
International Search Report and the Written Opinion dated Jun. 27, 2018 From the International Searching Authority Re. Application No. PCT/IB2018/051703. (12 Pages).
International Search Report and the Written Opinion dated Jun. 27, 2018 From the International Searching Authority Re. Application No. PCT/IB2018/051706. (11 Pages).

(Continued)

*Primary Examiner* — Deepak R Rao

(57) ABSTRACT

Disclosed herein are compounds for use in lightening skin, treating uneven skin pigmentation and/or improving the appearance of aging skin, as well as methods utilizing the compounds, and anti-aging compositions comprising the compounds and a pharmaceutically acceptable carrier. The compounds have the general Formula I:

Formula I or a pharmaceutically acceptable salt thereof, wherein the dashed line, X, Y, Z, Ra-Rd, and $R_1$-$R_3$ are as defined herein.

30 Claims, No Drawings

(56) References Cited

OTHER PUBLICATIONS

Gillbro et al. "The Melanogenesis and Mechanisms of Skin-Lightening Agents—Existing and New Approaches". International Journal of Cosmetic Science, 33(3): 210-221, Published Online Jan. 25, 2011.
Malathi et al. "Systemic Skin Whitening/Lightening Agents: What Is the Evidence?", Indian Journal of Dermatology, Venereology, and Leprology, 79(6): 842-846, Nov.-Dec. 2013.
Office Action dated Jan. 13, 2021 From the Israel Patent Office Re. Application No. 269327 and Its Translation Into English. (5 Pages).
Communication Pursuant to Article 94(3) EPC dated Feb. 1, 2021 From the European Patent Office Re. Application No. 18718504.6. (3 Pages).

USE OF HETEROCYCLIC COMPOUNDS IN THE TREATMENT OF PIGMENTED SKIN

RELATED APPLICATIONS

This application is a National Phase of PCT Patent Application No. PCT/IB2018/051703 having International filing date of Mar. 14, 2018, which claims the benefit of priority under 35 USC § 119(e) of U.S. Provisional Patent Application No. 62/470,898 filed on Mar. 14, 2017. The contents of the above applications are all incorporated by reference as if fully set forth herein in their entirety.

FIELD AND BACKGROUND OF THE INVENTION

The present invention, in some embodiments thereof, relates to the field of skin care, and more particularly, but not exclusively, to use of heterocyclic compounds in the treatment of pigmented skin.

Skin lightening products have become increasingly popular in the past few years. The main purpose of skin lightening products is to lighten or whiten the skin complexion (which is of particular interest in certain Asian populations) or to treat pigmentation disorders such as chloasma, freckles, pregnancy marks and age spots. Several types of skin lightening products are presently available.

Compounds described as skin lightening agents include hydroquinone and derivatives thereof, such as arbutin; kojic acid and derivatives thereof, such as kojic dipalmitate; azelaic acid; and flavonoids, such as aloesin, resveratrol and glabridin. Such compounds are generally administered topically in a lotion or gel, and are believed to act via inhibition of tyrosinase, which is involved in melanin synthesis [Gillbro & Olsson, *Int J Cosmet Sci* 2011, 33:210-221]. Additional topically administered compounds used as skin lightening agents include niacinamide, which has been reported to inhibit melanosome transfer; and retinoids such as tretinoin, and alpha hydroxy acids such as lactic acid and glycolic acid, which may remove superficial layers of skin cells where hyperpigmented cells can accumulate [Gillbro & Olsson, *Int J Cosmet Sci* 2011, 33:210-221].

Glutathione and trans-4-aminomethyl cyclohexane carboxylic acid have been marketed as systemic skin lightening agents, but evidence for their efficacy is lacking [Malathi & Thappa, *Indian J Dermatol Venerol Leprol* 2013, 79:842-846].

International Patent Application PCT/IB03/00134 (published as WO 03/063875) describes a use of cyclic nucleotide PDE5 (phosphodiesterase-5) inhibitors such as sildenafil for the reduction of or prevention of scarring and/or fibrosis in various tissues.

International Patent Application PCT/US2010/061054 (published as WO 2011/075655) describes a use of cyclic nucleotide phosphodiesterase inhibitors such as sildenafil for treating peripheral vascular disease, including Reynaud's syndrome.

International Patent Applications PCT/IL2007/000404 (published as WO 2007/110868), PCT/IL2007/001174 (published as WO2008/117269) and PCT/IL2011/050077 (published as WO 2012/140642) describe heterocyclic compounds which exhibit a dopamine receptor (e.g., D4 receptor) agonist activity and/or a PDE5 inhibitory activity, for use in the treatment of sexual disorders. International Patent Application PCT/IL2011/050077 (published as WO 2012/140642) further describes pharmaceutical compositions formulated for transdermal composition, which comprises the heterocyclic compound.

Additional background art includes International Patent Applications PCT/US2003/033400 (published as WO 2004/037183) and PCT/US2009/053040 (published as WO 2010/019450).

SUMMARY OF THE INVENTION

According to an aspect of some embodiments of the invention, there is provided a method of lightening skin in a subject in need thereof, the method comprising administering to the subject a therapeutically effective amount of a compound of the general Formula I:

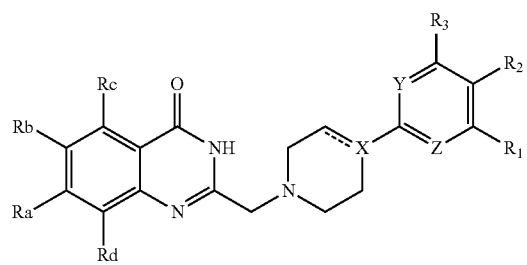

Formula I or a pharmaceutically acceptable salt thereof, wherein:

the dashed line denotes a saturated or non-saturated bond;

X is selected from the group consisting of CH, C and N, such that when X is C the dashed line denotes a non-saturated bond and when X is CH or N the dashed line denotes a saturated bond;

Y is N or $CR_4$;

Z is N or $CR_5$; and

Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted, thereby lightening the skin.

According to an aspect of some embodiments of the invention, there is provided a compound of the general Formula I, as defined hereinabove, or a pharmaceutically acceptable salt thereof, for use in lightening skin.

According to an aspect of some embodiments of the invention, there is provided a use of a compound of the general Formula I, as defined hereinabove, or a pharmaceutically acceptable salt thereof, in the manufacture of a medicament for lightening skin.

According to an aspect of some embodiments of the invention, there is provided a method of treating uneven skin pigmentation in a subject in need thereof, the method comprising administering to the subject a therapeutically effective amount of a compound of the general Formula I:

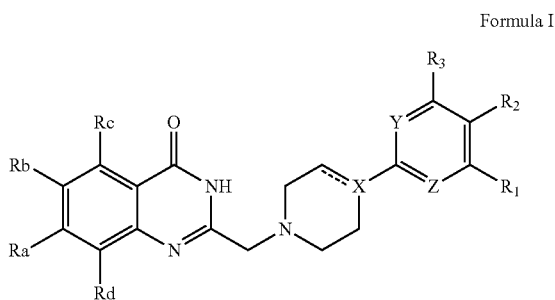

Formula I or a pharmaceutically acceptable salt thereof, wherein:

the dashed line denotes a saturated or non-saturated bond;

X is selected from the group consisting of CH, C and N, such that when X is C the dashed line denotes a non-saturated bond and when X is CH or N the dashed line denotes a saturated bond;

Y is N or $CR_4$;

Z is N or $CR_5$; and

Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted, thereby treating the uneven skin pigmentation.

According to an aspect of some embodiments of the invention, there is provided a compound of the general Formula I, as defined hereinabove, or a pharmaceutically acceptable salt thereof, for use in the treatment of uneven skin pigmentation.

According to an aspect of some embodiments of the invention, there is provided a use of a compound of the general Formula I, as defined hereinabove, or a pharmaceutically acceptable salt thereof, in the manufacture of a medicament for the treatment of uneven skin pigmentation.

According to an aspect of some embodiments of the invention, there is provided a method of improving the appearance of aging skin in a subject in need thereof, the method comprising administering to the subject a therapeutically effective amount of a compound of the general Formula I:

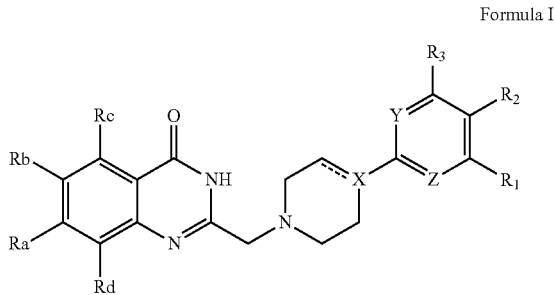

Formula I or a pharmaceutically acceptable salt thereof, wherein:

the dashed line denotes a saturated or non-saturated bond;

X is selected from the group consisting of CH, C and N, such that when X is C the dashed line denotes a non-saturated bond and when X is CH or N the dashed line denotes a saturated bond;

Y is N or $CR_4$;

Z is N or $CR_5$; and

Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted, thereby improving the appearance of the aging skin.

According to an aspect of some embodiments of the invention, there is provided a compound of the general Formula I, as defined hereinabove, or a pharmaceutically acceptable salt thereof, for use in a skin treatment for improving the appearance of aging skin.

According to an aspect of some embodiments of the invention, there is provided a use of a compound of the general Formula I, as defined hereinabove, or a pharmaceutically acceptable salt thereof, in the manufacture of a medicament for a skin treatment for improving the appearance of aging skin.

According to an aspect of some embodiments of the invention, there is provided an anti-aging composition comprising a compound of the general Formula I, as defined hereinabove, or a pharmaceutically acceptable salt thereof, and a pharmaceutically acceptable carrier, for use in improving the appearance of aging skin.

According to some embodiments of the invention, at least one of $R_1$-$R_5$ is selected from the group consisting of hydroxy and a moiety having the general Formula II:

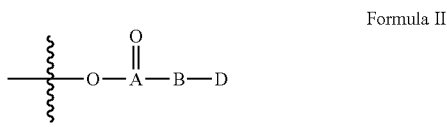

Formula II wherein:

A is selected from the group consisting of C and S=O;

B is absent or is a substituted or non-substituted, saturated or non-saturated alkylene chain; and D is selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted.

According to some embodiments of the invention, $R_1$ is selected from the group consisting of hydroxy and said moiety having the general Formula II.

According to some embodiments of the invention, A is a carbon atom.

According to some embodiments of the invention, $R_2$-$R_5$ are each hydrogen.

According to some embodiments of the invention, Ra-Rd are each hydrogen.

According to some embodiments of the invention, X is N.

According to some embodiments of the invention, Y is $CR_4$ and Z is $CR_5$.

According to some embodiments of the invention, the compound is 2-((4-(3-hydroxyphenyl)piperazin-1-yl)methyl)quinazolin-4-one:

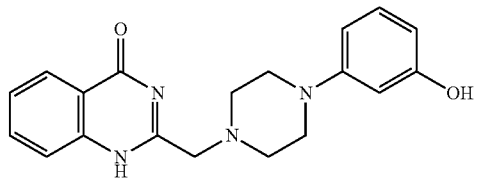

According to some embodiments of the invention, the administering comprises topical administration.

According to some embodiments of the invention, the compound forms a part of a pharmaceutical composition formulated for topical administration.

According to some embodiments of the invention, the abovementioned lightening skin is effected by topical administration of the compound.

According to some embodiments of the invention, the treatment is effected by topical administration of the compound.

According to some embodiments of the invention, the uneven skin pigmentation is associated with aging.

According to some embodiments of the invention, the uneven skin pigmentation is associated with age spots.

According to some embodiments of the invention, the anti-aging composition is formulated for topical administration.

According to some embodiments of the invention, the anti-aging composition is packaged in a packaging material and identified in print, in or on the packaging material, for use in improving the appearance of aging skin.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF SPECIFIC EMBODIMENTS OF THE INVENTION

The present invention, in some embodiments thereof, relates to the field of skin care, and more particularly, but not exclusively, to use of heterocyclic compounds in the treatment of pigmented skin.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While further studying the heterocyclic compounds and transdermal compositions described in International Patent Application PCT/IL2011/050077 (published as WO 2012/140642), the present inventors have serendipitously uncovered that such heterocyclic compounds can surprisingly reduce skin pigmentation and improve the appearance of skin.

The effect on skin was particularly surprising in that it was not limited to areas of the skin which were directly contacted with the compositions, unlike the effect of many compositions for treating skin.

According to an aspect of the present invention there is provided a compound of the general Formula I:

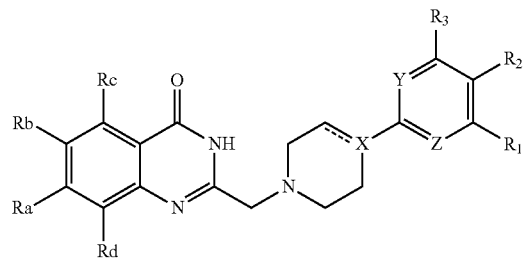

Formula I wherein X, Y, Z, Ra-Rd and $R_1$-$R_5$ are as defined herein (according to any of the respective embodiments described herein), for use in lightening skin.

According to another aspect of the present invention there is provided a use of a compound of the general Formula I (according to any of the embodiments described herein) in the manufacture of a medicament for lightening skin.

According to another aspect of the present invention there is provided a method of lightening skin in a subject in need thereof, the method comprising administering to the subject a therapeutically effective amount of a compound of the general Formula I (according to any of the embodiments described herein).

In some embodiments of any of the embodiments described herein relating to lightening skin, the method or use is for lightening a whole skin complexion.

In some embodiments of any of the embodiments described herein relating to lightening skin, the method or use is for lightening skin of a subject afflicted by uneven skin pigmentation, for example, skin comprising an uneven tone, melasma, skin discoloration, one or more acne marks and/or a scar.

According to an aspect of the present invention there is provided a compound of the general Formula I (according to any of the embodiments described herein) for use in treating uneven skin pigmentation.

According to another aspect of the present invention there is provided a use of a compound of the general Formula I (according to any of the embodiments described herein) in the manufacture of a medicament for treating uneven skin pigmentation.

According to another aspect of the present invention there is provided a method of treating uneven skin pigmentation in a subject in need thereof, the method comprising administering to the subject a therapeutically effective amount of a compound of the general Formula I (according to any of the embodiments described herein).

In some embodiments of any one of the embodiments described herein, the uneven skin pigmentation is associated with aging, for example, uneven skin tone which appears after the age of 30, and/or age spots.

In some embodiments of any one of the embodiments described herein relating to uneven skin pigmentation, the uneven skin pigmentation is associated with hyperpigmentation of skin, for example, melasma, chloasma, lentigo (e.g., solar lentigo), and/or one or more dark spots such as age spots and/or freckles.

In some embodiments of any one of the embodiments described herein, the uneven skin pigmentation is associated with a lack of pigmentation, for example, vitiligo. In such embodiments, lightening of the skin may beneficially reduce the contrast between pigmented regions and regions lacking pigmentation.

According to an aspect of the present invention there is provided a compound of the general Formula I (according to any of the embodiments described herein) for use in a skin treatment for improving the appearance of aging skin.

According to another aspect of the present invention there is provided a use of a compound of the general Formula I (according to any of the embodiments described herein) in the manufacture of a medicament for a skin treatment for improving the appearance of aging skin.

According to another aspect of the present invention there is provided a method of improving the appearance of aging skin in a subject in need thereof, the method comprising administering to the subject a therapeutically effective amount of a compound of the general Formula I (according to any of the embodiments described herein).

Herein, a "therapeutically effective amount" means an amount of one or more of the compounds of the present invention sufficiently effective to prevent, alleviate or ameliorate symptoms of a medical and/or cosmetic condition.

Administering the compound can be effected via a topical, transmucosal, oral, buccal, inhalation, parenteral and/or rectal route.

In some embodiments, the compound is administered topically.

In some embodiments, topical administration of the compound effects intradermal and/or transdermal administration of the compound.

As used herein the terms "transdermal" and "transdermally" refer to administration of a compound across the skin of a subject for systemic distribution.

As used herein the terms "intradermal" and "intradermally" refer to administration of a compound into the skin of a subject, wherein the compound spreads through the skin, thereby reaching areas other than the area to which the compound was initially administered.

In some embodiments of any of the embodiments described herein, the subject is preferably a mammal, more preferably a human.

In some embodiments of any of the embodiments described herein, administration of the compound according to any of the respective embodiments described herein enhances libido (e.g., in female subjects) in addition to treating skin as described herein. In some such embodiments, the compound is for use in concomitantly treating skin and enhancing libido.

Without being bound by any particular theory, it is believed that a compound according to some embodiments described herein may be capable of activating a physiological pathway (e.g., a pathway associated with a sex hormone, e.g., estrogen) which promotes both libido (e.g., in female subjects) and skin maintenance.

The compounds according to any of the embodiments presented herein can be utilized either per se, or, preferably, as a part of a pharmaceutical composition.

As used herein a "pharmaceutical composition" refers to a preparation of one or more of the compounds described herein, with other chemical components such as pharmaceutically acceptable and suitable carriers and excipients. The purpose of a pharmaceutical composition is to facilitate administration of a compound to an organism. The phrase "pharmaceutical composition" encompasses cosmeceutical compositions.

As used herein, the phrase "cosmeceutical composition" refers to a composition for topical administration as a cosmetic, which comprises a biologically active ingredient (e.g., the compound of Formula I, according to any of the respective embodiments described herein).

Compound Structure:

According to any of the aspects of embodiments of the present invention, the compound has the general Formula I:

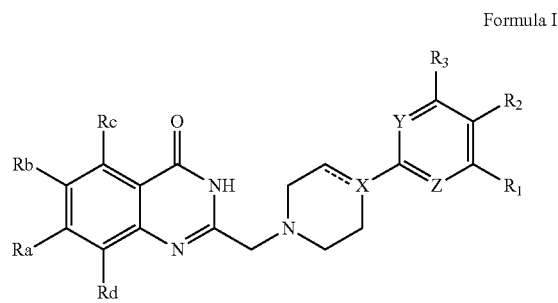

Formula I wherein:

the dashed line denotes a saturated or non-saturated bond;

X is CH, C or N such that when X is C the dashed line denotes a non-saturated bond and when X is CH or N the dashed line denotes a saturated bond;

Y is N or $CR_4$ (e.g., $CR_4$);

Z is N or $CR_5$ (e.g., $CR_5$); and

Ra-Rd, and $R_1$-$R_5$ are each independently hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and/or thiocarbamyl, each being substituted or non-substituted.

In some embodiments of any of the embodiments described herein, at least one of $R_1$-$R_5$ is hydroxy, a carboxy ester moiety or a sulfonate ester moiety, such that the aryl or heteroaryl ring comprising Y and Z is substituted by at least one hydroxy group, and/or at least one carboxy ester or sulfonate ester (which may be considered as derivatives of a hydroxy group). Carboxy and sulfonate ester moieties are described in more detail below. In some embodiments, $R_1$ is hydroxy, a carboxy ester or a sulfonate ester.

In some embodiments of any of the embodiments described herein, one of $R_1$-$R_5$ is hydroxy, a carboxy ester or a sulfonate ester, and the others are hydrogen. In some embodiments, $R_1$ is hydroxy, a carboxy ester or a sulfonate ester, and $R_2$-$R_5$ are hydrogen.

In some embodiments of any of the embodiments described herein, one or more of $R_1$-$R_5$ (optionally only one of $R_1$-$R_5$) is a substituent (i.e., a group other than hydrogen)

other than an ester moiety described herein. In some embodiments, the one or more substituent(s) is alkyl, hydroxy, alkoxy, halide and/or nitrile.

In some embodiments of any of the embodiments described herein, at least one of $R_1$-$R_5$ is hydroxy. In some embodiments, $R_1$ is hydroxy.

In some embodiments of any of the embodiments described herein, one of $R_1$-$R_5$ is hydroxy, and the others are hydrogen. In some embodiments, $R_1$ is hydroxy, and $R_2$-$R_5$ are hydrogen.

In some embodiments of any of the embodiments described herein, X is N, and the dashed line denotes a saturated bond.

In some embodiments of any of the embodiments described herein, the compound comprises a phenyl ring, wherein Y is $CR_4$ and Z is $CR_5$.

According to some embodiments, the bicyclic quinazolin-4-one moiety in Formula I is a non-substituted bicyclic moiety, such that each of Ra-Rd is hydrogen.

Alternatively, at least one of Ra-Rd is other than hydrogen, such that the bicyclic moiety is substituted.

In some embodiments, at least one of Ra-Rd is alkyl, hydroxy, alkoxy and/or halide.

In some embodiments, Ra is hydrogen or halide, short alkyl (being 1-4 carbon atoms in length) or short alkoxy (being 1-4 carbon atoms in length). In some embodiments, Ra is hydrogen or halide. In some embodiments, the halide is chloride. In some embodiments, the alkyl is ethyl. In some embodiments, the alkoxy is methoxy.

In some embodiments, Rb is hydrogen, halide (e.g., chloride), short alkyl (being 1-4 carbon atoms in length, and optionally being an aryl-substituted alkyl, e.g., benzyl), or alkoxy (being 1-4 carbon atoms in length, e.g., methoxy). In some embodiments, the alkyl is ethyl, propyl, trifluoromethyl or benzyl. In some embodiments, Rb is hydrogen, halide or alkoxy. According to exemplary embodiments, Rb is hydrogen or halide. In some embodiments, the halide is chloride. In some embodiments, the alkoxy is methoxy.

In some embodiments, Rc is hydrogen, alkoxy (being 1-4 carbon atoms in length), halide or alkyl (being 1-4 carbon atoms in length). In some embodiments, Rc is hydrogen, halide or alkyl. In some embodiments, the alkyl is methyl. In some embodiments, the halide is fluoride.

In some embodiments, Rd is hydrogen or alkyl. In some embodiments, the alkyl is methyl or propyl.

According to exemplary embodiments, Ra, Rc and Rd are each hydrogen.

R-55 (2-((4-(3-hydroxyphenyl)piperazin-1-yl)methyl) quinazolin-4-one) is an exemplary compound suitable for use according to embodiments of the invention.

Additional examples of compounds having general Formula I, which are suitable for use according to embodiments of the invention, as well as processes for preparing such compounds, are presented in International Patent Application Publication WO 2012/140642, the contents of which are incorporated herein in their entirety.

Each of the compounds described herein can further be in a form of a pharmaceutically acceptable salt thereof.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of the present embodiments, a pharmaceutically acceptable salt of the compounds described herein may optionally be an acid addition salt comprising at least one amine group of the compound (e.g., an amine group in a piperazine moiety) which is in a form of an ammonium ion (e.g., a quaternary ammonium ion), in combination with at least one counter ion, derived from the selected acid, that forms a pharmaceutically acceptable salt.

Depending on the stoichiometric proportions between the base (the amine group(s)) and the acid in the salt, the acid additions salts can be either mono-addition salts or poly-addition salts.

The phrase "mono-addition salt", as used herein, refers to a salt in which the stoichiometric ratio between the acid anion and amine cation is 1:1, such that the acid addition salt includes one molar equivalent of the acid per one molar equivalent of the compound.

The phrase "poly-addition salt", as used herein, refers to a salt in which the stoichiometric ratio between the acid anion and the amine cation is greater than 1:1 and is, for example, 2:1, 3:1, 4:1 and so on, such that the acid addition salt includes two or more molar equivalents of the acid per one molar equivalent of the compound.

The acid addition salts of the compounds described herein are therefore complexes formed between one or more amino groups of the drug and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined hereinabove.

Further, each of the compounds described herein, including the salts thereof, can be in a form of a solvate or a hydrate thereof.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The present embodiments further encompass any stereoisomers (enantiomers and diastereomers) of the compounds described herein, as well as any isomorph thereof.

Esters:

In some embodiments of any one of the embodiments described herein, at least one of $R_1$-$R_5$ is an ester moiety, for example, a carboxy or sulfonate which is a carboxy ester or sulfonate ester, respectively. Such compounds are referred to herein also as "esterified compounds".

In some embodiments of any one of the embodiments described herein, the esterified compound is an esterified derivative of R-55, differing from R-55 only in that an ester moiety (according to any of the respective embodiments described herein) is present at the $R_1$ position instead of a hydroxy group. Additional examples of esterified compounds having general Formula I, which are suitable for use according to embodiments of the invention, are presented in International Patent Application Publication WO 2012/140642.

In some embodiments of any one of the embodiments described herein, the ester moiety has the general Formula II:

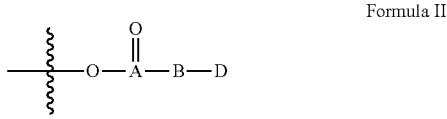

Formula II wherein:

A is selected from the group consisting of a carbon atom and S=O;

B is absent or is a substituted or non-substituted, saturated or non-saturated alkylene chain; and D is selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted.

In some embodiments, D is alkyl. The alkyl is optionally non-substituted.

In some embodiments, D is alkenyl, for example, non-substituted alkenyl.

Without being bound by any particular theory, it is believed that the ester moiety of the esterified compound undergoes gradual hydrolysis in vivo, to release an active compound comprising a hydroxy group in place of the ester moiety. It is further believed that the active compound comprising a hydroxy group, while being therapeutically effective in vivo, is limited by a relatively low availability in plasma following oral administration, and that the esterified compound provides a considerably higher availability (e.g., oral bioavailability) in plasma.

As used herein, an "alkylene chain" refers to a bi-radical moiety (i.e., a divalent radical) comprising 1-20 carbon atoms covalently linked to one another by single, double or triple bonds. In a "saturated" alkylene chain, the carbon atoms are linked to one another solely by single bonds, whereas an "unsaturated" alkylene chain comprises at least one double bond and/or triple bond between carbon atoms. The alkylene chain is optionally substituted by one or more substituents, whereby the substituents can be, for example, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, nitrile, nitro, azide, phosphonyl, phosphinyl, oxo, carbonyl, thiocarbonyl, urea, thiourea, carbamyl, N-carbamyl, O-thiocarbamyl, N-thiocarbamyl, C-amido, N-amido, C-carboxy, O-carboxy, sulfonamido, and amino, as these terms are defined herein. Optionally, B is an alkylene chain of up to 10 carbon atoms, optionally of up to 4 carbon atoms (e.g., a saturated alkylene of 1 to 4 carbon atoms), and optionally 1 or 2 carbon atoms. Optionally, B is a saturated alkylene chain, and the saturated alkylene is optionally non-substituted (e.g., $CH_2$, $CH_2CH_2$). Alternatively, the saturated alkylene chain may be substituted. In some embodiments, the saturated alkylene chain is substituted by hydroxy.

In some embodiments of any one of the embodiments described herein, the esterified compound is part of a pharmaceutical composition formulated for oral administration, according to any of the respective embodiments described herein.

As described in International Patent Application Publication WO 2012/140642, the rate of release of the active therapeutic agent (e.g., by hydrolysis of the esterified compound) can be controlled by selection of an appropriate ester moiety. Thus, for example, carboxy esters comprising small unsubstituted moieties (e.g., alkyl, cycloalkyl, aryl or heteroaryl) resulted in relatively rapid hydrolysis (e.g., wherein $T_{1/2}$ in human plasma is about 150 minutes or less), whereas sulfonate ester moieties resulted in relatively slow hydrolysis (e.g., wherein the half-life ($T_{1/2}$) in human plasma is over 1000 minutes or less).

Thus, the half-life in human plasma may optionally be manipulated as desired by selecting a carboxy ester (for shorter half-lives) or a sulfonate ester (for longer half-lives).

Thus, in some embodiments, the ester is a sulfonate ester, for example, an alkyl-substituted sulfonate ester or an aryl-substituted sulfonate ester. Methanesulfonate is a non-limiting example of a suitable alkyl-substituted sulfonate ester moiety and p-toluenesulfonate is non-limiting example of a suitable aryl-substituted ester moiety.

In some embodiments of any one of the embodiments described herein, the ester moiety is carboxy (i.e. A is a carbon atom) rather than sulfonate (wherein A is S=O).

For some applications relating to skin, a very short (e.g., less than 10 minutes, less than 30 minutes, less than 60 minutes) $T_{1/2}$ in human plasma at 37° C. (e.g., as is typical of small carboxy esters such as propionate ester, wherein B is absent and D is ethyl) is undesirable.

Without being bound by any particular theory, it is believed that an active agent comprising a hydroxy group (e.g., formed upon hydrolysis of an esterified compound described herein) is more susceptible to partial or complete inactivation and/or clearance from the body, due to metabolic processes in vivo (e.g., by glucuronidation and/or sulfation of the hydroxy group). It is further believed that rapid hydrolysis may result in considerable inactivation and/or clearance from the body before the active agent reaches the skin.

In some embodiments of any one of the embodiments described herein, the ester moiety is terminated by a moiety (represented by variable D) which is relatively bulky, i.e., wherein D comprises at least 3 carbon atoms and/or heteroatoms, optionally at least 4, and optionally at least 5 carbon atoms and/or heteroatoms, optionally such that D is alkyl, alkenyl or alkynyl and B is absent. In some embodiments, the bulky moiety is a non-linear group, comprising for example, a branched moiety (e.g., branched alkyl, alkenyl or alkynyl) and/or a cyclic moiety. In some embodiments, the alkyl, alkenyl or alkynyl group is devoid of an aryl, heteroaryl, heteroalicyclic or cycloalkyl substituent.

In some embodiments, the bulky moiety (represented by variable D) is a cyclic moiety selected from the group consisting of cycloalkyl, heteroalicyclic, aryl and heteroaryl, each being substituted or non-substituted.

As described in International Patent Application Publication WO 2012/140642, ester moieties comprising aryl and heteroaryl tend to exhibit an advantageous half-life in human plasma (e.g., in a range of from 2 to 8 hours), wherein the half-life depends on whether a substituent is present, and on the nature (e.g., size) of the substituent, if present.

For example, compounds comprising a non-substituted aryl (e.g., phenyl) or heteroaryl (e.g., pyrrol-2-yl) moiety exhibit a half-life in human plasma of at least about 2 hours, whereas compounds comprising non-substituted cycloalkyl (e.g., cyclohexyl) exhibit a considerably shorter half-life.

In some embodiments of any one of the embodiments described herein, a substituent of an aryl or heteroaryl is selected from the group consisting of alkyl, alkoxy, aryloxy, hydroxy, amine, nitrile, nitro and halide. In some embodiments, an aryl group is substituted with the aforementioned substituent(s).

As further described in International Patent Application Publication WO 2012/140642, ring substituents (e.g., phenyl substituents) slow hydrolysis considerably, to a degree which is correlated to the size of the substituent.

In some embodiments of any one of the embodiments described herein, the substituent is small, for example, 1 or 2 atoms in size (excluding hydrogen atoms). Examples of such substituents include methyl, ethyl, methoxy, hydroxy, amino ($-NH_2$), nitrile and halide (fluoro or chloro, in some embodiments). Small substituents may lengthen the half-life of the esterified compound to a significant, but not excessive extent. Thus, for example, compounds having such substituents of 1 or 2 atoms tend to have half-lives in human plasma of up to about 8 hours (480 minutes), whereas larger substituents (e.g., ethoxy) may have considerably longer half-lives (e.g., >1000 minutes).

In some embodiments of any one of the embodiments described herein, the aryl, heteroaryl, heteroalicyclic or cycloalkyl is attached directly to A, wherein B is absent (e.g., such that the ester moiety is benzoyl or a derivative thereof).

In some embodiments of any one of the embodiments described herein, the aryl, heteroaryl or cycloalkyl is attached via a saturated or unsaturated alkylene chain represented by the variable B (e.g., such that the ester moiety is phenylacetyl or a derivative thereof).

As described in International Patent Application Publication WO 2012/140642, such alkylene chains generally do not exhibit a tendency to slow hydrolysis.

Pharmaceutical Composition:

As mentioned hereinabove, the compounds according to any of the embodiments presented herein can be utilized either per se, or, preferably, as a part of a pharmaceutical composition.

According to another aspect of embodiments of the invention, there is provided an anti-aging composition comprising a compound having general Formula I (according to any of the respective embodiments described herein), and a pharmaceutical carrier, for use in lightening skin, treating uneven pigmentation and/or improving the appearance of aging skin, according to any of the respective embodiments described herein.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein, the terms "pharmaceutical" and "pharmaceutically" refer to any compound and/or composition intended for beneficially altering a condition and/or behavior of at least a portion of the body (e.g., skin), including cosmetically altering, e.g., the skin. It is to be appreciated that such a definition may be broader than the use of such terms by regulatory agencies, which may exclude, for example, cosmetic effects from the scope of the terms.

In some embodiments of any of the embodiments described herein, the pharmaceutical composition is a cosmetic composition which alters the skin (as opposed, for example, to cosmetic compositions, e.g., make-up, which merely mask the skin).

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Examples of suitable solid or gel phase carriers or excipients include, but are not limited to, calcium carbonate, calcium phosphate, various sugars, starches, cellulose derivatives, gelatin and polymers such as polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions described herein according to various embodiments of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the abovementioned compounds into preparations which, can be used pharmaceutically. Proper formulation is dependent upon the route of administration chosen.

According to some embodiments of any of the embodiments described herein, the pharmaceutical composition is formulated for topical administration, and optionally for intradermal and/or transdermal administration.

As exemplified in the Examples section below, pharmaceutical compositions formulated for topical administration, such as are described herein, allow the compound to exhibit a desired activity (e.g., as described herein) over a large area of skin.

Additional pharmaceutical compositions formulated for topical (e.g., transdermal) administration of compounds described herein, which may be used for treating skin according to any of the respective embodiments described herein, are disclosed in International Patent Application Publication WO 2012/140642.

Without being bound by any particular theory, it is believed that topical administration provides gradual uptake into the skin and/or bloodstream over the course of a considerable time period, and can therefore provide a long lasting, therapeutically effective concentration of the compound in the body, even if the compound has a relatively short half-life in plasma.

A topical formulation may be formulated with any of a variety of compounds, including, but not limited to, esterified compounds (as described herein). Thus, for example, the advantageous effect of the topical formulation may be used in addition to, or instead of, the advantageous effect of the ester moiety described herein.

By selecting the appropriate carrier and optionally other ingredients that can be included in the composition, as is detailed herein, the pharmaceutical compositions described herein may be formulated into any form suitable for topical application. Hence, the pharmaceutical compositions can be, for example, in a form of a cream, an ointment, a paste, a gel, a lotion, and a soap. Ointments are semisolid preparations, typically based on vegetable oil (e.g., shea butter and/or cocoa butter), petrolatum or petroleum derivatives. As with other carriers or vehicles, an ointment base should be inert, stable, nonirritating and nonsensitizing.

Lotions are preparations that may to be applied to the skin without friction. Lotions are typically liquid or semiliquid preparations with a water or alcohol base, for example, an emulsion of the oil-in-water type. Lotions are typically preferred for treating large areas, due to the ease of applying a more fluid composition.

Creams are viscous liquids or semisolid emulsions, either oil-in-water or water-in-oil. Cream bases typically contain an oil phase, an emulsifier and an aqueous phase. The oil phase, also called the "lipophilic" phase, optionally comprises petrolatum and/or a fatty alcohol such as cetyl or stearyl alcohol. The aqueous phase optionally contains a humectant. The emulsifier in a cream formulation is optionally a nonionic, anionic, cationic or amphoteric surfactant.

Pastes are semisolid dosage forms which, depending on the nature of the base, may be a fatty paste or a paste made from a single-phase aqueous gel. The base in a fatty paste is generally petrolatum, hydrophilic petrolatum and the like. The pastes made from single-phase aqueous gels generally incorporate carboxymethylcellulose or the like as a base.

Gel formulations are semisolid, suspension-type systems. Single-phase gels contain organic macromolecules distributed substantially uniformly throughout the carrier liquid, which is typically aqueous, but also, preferably, contains a non-aqueous solvent and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol®. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

A pharmaceutical composition formulated for topical (e.g., intradermal and/or transdermal) administration may optionally be present in a patch, a swab, a pledget, and/or a pad.

Dermal patches and the like may comprise some or all of the following components: a pharmaceutical composition (e.g., as described herein), a liner for protecting the patch during storage, which is optionally removed prior to use, an adhesive for adhering different components together and/or adhering the patch to the skin, a backing which protects the patch from the outer environment, and/or a membrane which controls release of a drug into the skin.

According to optional embodiments, the pharmaceutical composition is in a form of a water-in-oil emulsion. The water-in-oil emulsion may be, for example, in the form of a cream.

As used herein and in the art, a "water-in-oil emulsion" is an emulsion characterized by an aqueous phase which is dispersed within a lipophilic phase.

Herein, the term "emulsion" refers to a composition comprising liquids in two or more distinct phases (e.g., a hydrophilic phase and a lipophilic phase). Non-liquid substances (e.g., dispersed solids and/or gas bubbles) may optionally also be present.

In some embodiments of any of the embodiments described herein, the composition comprises at least one suitable solvent, for example, a solvent suitable for a lipophilic phase of an emulsion (according to any of the respective embodiments described herein). The one or more solvent may optionally be combined with one or more additional ingredients, such as surfactants, solubilizing agents and/or sustained release agents (e.g., according to any of the respective embodiments described herein).

Examples of suitable solvents include, without limitation, alkylene glycols (e.g., ethylene glycol, propylene glycol, butylene glycol) and alkane diols (e.g., propane-1,3-diol), and fatty acid esters thereof (e.g., propylene glycol laurate, propylene glycol monolaurate).

According to some embodiments, the lipophilic phase of the emulsion comprises propylene glycol, propylene glycol monolaurate (e.g., Lauroglycol™ 90) and/or propylene glycol laurate (e.g., Lauroglycol™ FCC), for example, as a solvent.

Examples of suitable surfactants, solubilizing agents and/or sustained release agents include, without limitation, phospholipids (e.g., phosphatidyl choline, phosphatidyl ethanolamine, phosphatidyl serine, phosphatidyl inositol and phosphatidic acid) and fatty acid esters of glycerol and/or polyethylene glycol (macrogol). Phosphatidyl choline is an exemplary phospholipid, and caprylocaproyl macrogolglycerides, lauroyl macrogolglycerides and stearoyl macrogolglycerides are exemplary fatty acid esters of glycerol and macrogol (optionally in the form of a mixture of glycerol and macrogol esters).

In some embodiments, the lipophilic phase further comprises at least one solubilizing agent, for example, lauroyl macrogolglycerides (e.g., lauroyl macrogol-32 glycerides), which are also known in the art as lauroyl polyoxyl glycerides. Exemplary lauroyl macrogolglycerides are available as Gelucire® 44/14.

In some embodiments, the composition further comprises at least one surfactant, for example, phosphatidyl choline and/or caprylocaproyl macrogolglycerides (e.g., caprylocaproyl polyoxyl-8 glycerides). Exemplary caprylocaproyl macrogolglycerides are available as Labrasol®.

In some embodiments, the composition further comprises macrogolglycerol stearate (e.g., stearoyl macrogol-32 glycerides), which are also known in the art as stearoyl macrogolglycerides or stearoyl polyoxyl glycerides. Exemplary macrogolglycerol stearate is available as Gelucire® 50/13.

The solvent and/or additional components of the emulsion (e.g., such as described herein) are optionally selected so as to allow for at least a desired solubility (optionally, at least 10 mg per 1 gram) of a compound described herein in the composition.

The solvent and additional components are preferably selected so as to be non-toxic when applied topically (e.g., intradermally and/or transdermally).

In some embodiments, the emulsion comprises from 60 to 97.5 weight percents of a lipophilic phase, and optionally from 70 to 90 weight percents.

Herein, ingredients of the composition which are soluble in a lipophilic phase are considered components of the lipophilic phase (regardless of whether the ingredient undergoes partitioning between a lipophilic phase and the aqueous phase). Similarly, a weight percent of a lipophilic phase refers herein to a sum of the weights of the components of the lipophilic phase, as defined herein.

According to optional embodiments, the lipophilic phase of the composition comprises propylene glycol, propylene glycol monolaurate (e.g., Lauroglycol™ 90), lauroyl macrogolglycerides (e.g., Gelucire® 44/14), phosphatidyl choline, caprylocaproyl macrogolglycerides (e.g., Labrasol®) and macrogolglycerol stearate (Gelucire® 50/13).

In an exemplary embodiment, the composition as a whole comprises from 25 to 75 weight percents propylene glycol, from 8 to 30 weight percents lauroyl macrogolglycerides (e.g., Gelucire® 44/14), from 1 to 4 weight percents caprylocaproyl macrogolglycerides (e.g., Labrasol®), from 1 to 4 weight percents propylene glycol monolaurate (e.g., Lauroglycol™ 90), from 2.5 to 10 weight percents macrogolglycerol stearate (e.g., Gelucire® 50/13), and from 3 to 12 weight percents phosphatidyl choline.

According to optional embodiments, the composition further comprises vitamin E TPGS (α-tocopheryl polyethylene glycol succinate), for example, at a concentration of up to 1 weight percent of the composition.

In some embodiments, the composition further comprises a sustained-release agent (e.g., a water-soluble sustained-release agent in the aqueous phase of the emulsion). Suitable sustained-release agents are commercially available. Optionally, the sustained-release agent is a thickening agent (optionally a gelling agent described herein).

As exemplified herein, pharmaceutical compositions formulated for topical administration as described herein may comprise a relatively high concentration of a compound described herein (e.g., a compound having Formula I), for example, a concentration of at least 10 mg of the compound per 1 gram of the pharmaceutically effective carrier therein.

According to optional embodiments, the pharmaceutical composition is stable (e.g., devoid of substantial chemical changes and/or phase separation) at room temperature (e.g., 20° C.) for at least 2 weeks, optionally at least 1 month, optionally at least 2 months, optionally at least 6 months, and optionally at least 1 year.

As described herein, topical pharmaceutical compositions described herein may provide for a continuous release of the compound into the body of a subject. In some embodiments, the pharmaceutical composition is characterized by an ability to release the compound (e.g., a compound according to Formula I) for at least 2 hours, optionally for at least 3 hours, optionally for at least 4 hours, and optionally for at least 6 hours, upon administration of the composition on a skin of a subject.

Release of a compound from an applied composition may be determined quantitatively by any suitable technique used in the art.

Optionally, the release is determined in vivo, by monitoring plasma concentrations of the compound. Using standard pharmacokinetic analysis, the absorption of a compound into the plasma may be determined for each point in time, based on the observed concentration of the compound in plasma and on the rate of clearance of the compound.

Alternatively, the release may be determined in vitro, by monitoring permeation of a compound through skin in a Franz diffusion cell.

Herein, a composition is considered to be able to release a compound for a particular period of time (e.g., at least two hours) if the rate at which the compound permeates the skin (e.g., absorption into plasma) during the period of time is at least half of the maximal rate achieved after administration of the composition.

Compounds of embodiments of the invention may be formulated for routes of administration other than topical administration.

For oral administration, the compounds of embodiments of the invention can be formulated readily by combining the compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP).

If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

The compounds of the present invention may also be formulated in rectal compositions such as suppositories or retention enemas, using, e.g., conventional suppository bases such as cocoa butter or other glycerides.

The compounds described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the compounds of the present invention prepared in water-soluble form. Additionally, suspensions of the compounds may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds to allow for the preparation of highly concentrated solutions.

Alternatively, the compounds of the present invention may be in powder form for constitution with a suitable vehicle, e.g., sterile, pyrogen-free water, before use.

For injection, the compounds of embodiments of the invention may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For administration by inhalation, the compounds for use according to the present invention are conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compounds of the present invention and a suitable powder base such as, but not limited to, lactose or starch.

Pharmaceutical compositions suitable for use in context of embodiments of the present invention include compositions wherein the active ingredients are contained in a therapeutically effective amount for achieving the intended purpose.

Determination of a therapeutically effective amount is well within the capability of those skilled in the art, especially in light of the detailed disclosure provided herein.

Toxicity of the compounds described herein can be determined by standard pharmaceutical procedures in experimental animals, e.g., by determining the $LD_{50}$ (lethal dose causing death in 50% of the tested animals) for a subject compound. The data obtained from these animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active moiety which are sufficient to maintain the desired effects, termed the minimal effective concentration (MEC). The MEC will vary for each preparation, but can be estimated from, e.g., the concentration necessary in plasma to achieve, over a given period of time, a desired effect in the skin of human subjects. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

The amount of a composition to be administered will, of course, be dependent on the subject being treated, the severity of the affliction, the manner of administration, the judgment of the prescribing physician, etc.

The amount of the compound to be administered can depend on the pharmacokinetics of the compound, for example, a half-life of the administered compound and/or a product of hydrolysis of the administered compound in plasma, and/or a rate of absorption of an administered compound (e.g., when administered topically).

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of skin (e.g., according to any of the embodiments described herein).

Thus, according to some embodiments of the present invention, the pharmaceutical compositions described herein are packaged in a packaging material and identified in print, in or on the packaging material, for use in the lightening skin, treating uneven skin pigmentation and/or improving the appearance of aging skin (e.g., as described herein) in a subject in need thereof.

Miscellaneous Definitions

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthyl and anthracenyl. Phenyl and naphthyl are exemplary aryl groups. The aryl group may be substituted or non-substituted. Exemplary non-substituted aryl groups include non-substituted phenyl and naphthyl. When an aryl is substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, nitrile, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazine, pyrazole, pyridine, pyrimidine, benzopyrone (e.g., 4-oxo-1-benzopyran), quinoline, isoquinoline and purine. Pyrrole, thiazole, pyrazine and 4-oxo-1-benzopyran are exemplary heteroaryl groups. The heteroaryl group may be substituted or non-substituted. When a heteroaryl is substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, nitrile, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. It is to be appreciated that a substituent (e.g., oxo) may be a component of the conjugated pi-electron system.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropyl, cyclobutyl, cyclopentyl, cyclopentenyl, cyclohexyl, cyclohexadiene, cycloheptyl, cycloheptatrienyl, norbornyl (i.e., bicyclo[2.2.1]heptanyl) and adamantyl. Exemplary cycloalkyl groups include cyclopropyl, cyclobutyl, cyclohexyl, norbornyl and adamantyl. A cycloalkyl group may be substituted or non-substituted. Exemplary non-substituted cycloalkyl groups include cyclopropyl, cyclopentyl, cyclohexyl, and adamantyl. When a cycloalkyl is substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, nitrile, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, nitrile, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Representative examples are piperidine, piperazine, tetrahydrofuran, tetrahydropyran, morpholine and the like.

As used herein throughout, the term "alkyl" refers to a saturated aliphatic hydrocarbon including straight chain and branched chain groups. Preferably, the alkyl group has 1 to 20 carbon atoms. Whenever a numerical range, e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfonate, nitrile, nitro, azide, phosphonyl, phosphinyl, oxo, carbonyl, thiocarbonyl, urea, thiourea, carbamyl, N-carbamyl, O-thiocarbamyl, N-thiocarbamyl, C-amido, N-amido, C-carboxy, O-carboxy, sulfonamido, and amino, as these terms are defined herein.

An "alkenyl" group refers to an unsaturated aliphatic hydrocarbon which comprises at least one carbon-carbon double bond, including straight chain and branched chain groups. Preferably, the alkenyl group has 2 to 20 carbon atoms. More preferably, the alkenyl is a medium size alkenyl having 2 to 10 carbon atoms. Most preferably, unless otherwise indicated, the alkenyl is a lower alkenyl having 2 to 5 carbon atoms. The alkenyl group may be substituted or unsubstituted. When substituted, the substituent group can be, for example, cycloalkyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfonate, nitrile, nitro, azide, phosphonyl, phosphinyl, oxo, carbonyl, thiocarbonyl, urea, thiourea, carbamyl, N-carbamyl, O-thiocarbamyl, N-thiocarbamyl, C-amido, N-amido, C-carboxy, O-carboxy, sulfonamido, and amino, as these terms are defined herein.

An "alkynyl" group refers to an unsaturated aliphatic hydrocarbon which comprises at least one carbon-carbon triple bond, including straight chain and branched chain groups. Preferably, the alkynyl group has 2 to 20 carbon atoms. More preferably, the alkynyl is a medium size alkynyl having 2 to 10 carbon atoms. Most preferably, unless otherwise indicated, the alkynyl is a lower alkynyl having 2 to 4 carbon atoms. The alkynyl group may be substituted or unsubstituted. When substituted, the substituent group can be, for example, cycloalkyl, alkenyl, aryl, heteroaryl, heteroalicyclic, halo, hydroxy, alkoxy, aryloxy, thiohydroxy, thioalkoxy, thioaryloxy, sulfinyl, sulfonyl, sulfonate, nitrile, nitro, azide, phosphonyl, phosphinyl, oxo, carbonyl, thiocarbonyl, urea, thiourea, carbamyl, N-carbamyl, O-thiocarbamyl, N-thiocarbamyl, C-amido, N-amido, C-carboxy, O-carboxy, sulfonamido, and amino, as these terms are defined herein.

As used herein, the terms "amine" and "amino" refer to a —NR'R" group, wherein R' and R" are selected from the group consisting of hydrogen, alkyl, cycloalkyl, heteroalicyclic (bonded through a ring carbon), aryl and heteroaryl (bonded through a ring carbon). Optionally, R' and R" are selected from the group consisting of hydrogen and alkyl comprising 1 to 4 carbon atoms. Optionally, R' and R" are hydrogen.

A "hydroxy" group refers to an —OH group.

An "azide" group refers to a —N=N$^+$=N$^-$ group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "disulfide" group refers to both a —S-thioalkoxy and a —S-thioaryloxy group.

A "carbonyl" group refers to a —C(=O)—R' group, where R' is defined as hereinabove.

A "thiocarbonyl" group refers to a —C(=S)—R' group, where R' is as defined herein.

A "carboxy" group encompasses C-carboxy and O-carboxy groups, as defined herein.

A "C-carboxy" group refers to a —C(=O)—O—R' group, where R' is as defined herein.

An "O-carboxy" group refers to an R'C(=O)—O— group, where R' is as defined herein.

A "carboxylic acid" group refers to a C-carboxy group in which R' is hydrogen.

A "thiocarboxy" or "thiocarboxylate" group refers to both —C(=S)—O—R' and —O—C(=S)R' groups.

A "sulfonate" group refers to both —S(=O)$_2$—O—R' and —O—S(=O)$_2$—R' groups, where R' is as defined herein.

An "ester" refers herein to both carboxy esters and sulfonate esters.

A "carboxy ester" refers to an O-carboxy group attached to a carbon atom.

A "sulfonate ester" refers to a —O—S(=O)$_2$—R' sulfonate group attached to a carbon atom.

A "halide" or "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

An "O-thiocarbamyl"" group refers to an —OC(=S)—NR'R" group, where each of R' and R" is as defined herein.

An "N-thiocarbamyl" group refers to an R'OC(=S)NR"— group, where each of R' and R" is as defined herein.

A "thiocarbamyl" or "thiocarbamate" group encompasses O-thiocarbamyl and N-thiocarbamyl groups.

A thiocarbamate bond describes a —O—C(=S)—NR'— bond, where R' is as described herein.

A "C-amido" group refers to a —C(=O)—NR'R" group, where each of R' and R" is as defined herein.

An "N-amido" group refers to an R'C(=O)—NR"— group, where each of R' and R" is as defined herein.

An "amide" group encompasses both C-amido and N-amido groups.

A "nitro" group refers to an —NO$_2$ group.

A "nitroso" group refers to an —NO group.

A "nitrile" or "cyano" group refers to a —C≡N group.

An "isonitrile" group refers to a —N≡C group.

An "oxo" group refers to a =O group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

The term "phosphinyl" describes a —PR'R" group, with each of R' and R" as defined hereinabove.

A "urea" group refers to an —N(R')—C(=O)—NR"R'" group, where each of R' and R" is as defined herein, and R'" is defined as R' and R" are defined herein.

The term "thiourea" describes a —N(R')—C(=S)—NR"— group, with each of R' and R" as defined hereinabove.

As used herein, the term "epoxide" describes a

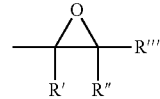

group, where R', R" and R'" are as defined herein.

As used herein, the term "thiirane" describes a group that is equivalent to an epoxide, wherein the oxygen atom of the epoxide is replaced with a sulfur atom.

As used herein, the term "aziridine" describes a group that is equivalent to an epoxide, wherein the oxygen atom of the epoxide is replaced with a nitrogen atom, and the nitrogen atom binds, in addition to two adjacent carbon atoms, R"", wherein R"" is defined according to the same definition as R'.

The term "hydrazine", as used herein, describes a —NR'—NR"R'" group, with R', R" and R'" as defined herein.

As used herein the terms "treating", "treatment" and any grammatical diversion thereof include abrogating, substantially inhibiting, slowing or reversing the progression of a condition, substantially ameliorating clinical or aesthetical symptoms of a condition or substantially preventing the appearance of clinical or aesthetical symptoms of a condition. The condition may be a cosmetic condition and/or a medical condition.

As used herein the term "about" refers to ±10%.

The terms "comprises", "comprising", "includes", "including", "having" and their conjugates mean "including but not limited to".

The term "consisting of" means "including and limited to".

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:
Carbopol® Ultrez 10 (cross-linked polyacrylic acid) was obtained from Noveon Inc. (USA);
Gelucire® 44/14 (lauroyl polyoxyl-32 glycerides) was obtained from Gattefosse (France);
Gelucire® 50/13 (macrogolglycerol stearates) was obtained from Gattefosse;
Labrasol® (caprylocaproyl polyoxyl-8 glycerides) was obtained from Gattefosse;
Lauroglycol™ 90 (propylene glycol monolaurate) was obtained from Gattefosse;
Phosphatidyl choline was obtained from Lipoid (Germany);

Propylene glycol was obtained from MP Biomedical (France); and
Vitamin E TPGS (α-tocopheryl polyethylene glycol succinate) was obtained from Eastman (UK).
R-55 (2-((4-(3-hydroxyphenyl)piperazin-1-yl)methyl) quinazolin-4-one) was synthesized as described in International Patent Application Publication WO 2012/140642.

Effect of Topical Application of R-55 on Skin:
A formulation for topical administration of R-55 (2-((4-(3-hydroxyphenyl)piperazin-1-yl)methyl)quinazolin-4-one) was prepared, comprising 10 mg/ml R-55.

A lipid-based phase was formed which consisted primarily of propylene glycol (a solvent of R-55 and penetration enhancer), along with Gelucire® 44/14 lauroyl macrogolglycerides (a solubilizer of R-55), Gelucire® 50/13 stearoyl macrogolglycerides (a sustained release agent), phosphatidyl choline (a surfactant), Labrasol® caprylocaproyl macrogolglycerides (a co-surfactant and penetration enhancer), Lauroglycol™ 90 (a solubilizer of R-55, co-surfactant and penetration enhancer), and vitamin E TPGS (a stabilizer). The ingredients were mixed by stirring at a temperature in a range of from 40° C. to 60° C. until the phosphatidyl choline and R-55 were completely dissolved, as indicated by obtaining a clear solution.

An aqueous solution of a carbomer (Carbopol® Ultrez 10) was added to the lipid-based phase with R-55 to obtain 100 grams of a suspension, which was stirred continuously at room temperature. A gel-like water-in-oil emulsion was formed, with relatively round aqueous droplets dispersed in a lipophilic phase, and the emulsion was stable for at least 2 weeks at room temperature.

Two middle-aged Caucasian female volunteers self-administered R-55 by applying daily the topical formulation of R-55 at discrete locations on the face and behind the ear.

No red marks were observed on the skin after application, suggesting that the formulation does not significantly enhance local blood flow and is not inflammatory.

After about one month of daily usage, the skin of the subjects was noticeably less pigmented, and had an overall fresher, younger appearance. This effect was not limited to skin upon which the formulation was applied, indicating that intradermal and/or transdermal administration of the compound was effected.

Safety and Toxicology Studies:
A formulation for topical administration of R-55 (10 mg/ml), prepared as described hereinabove, was tested for the presence of substances prohibited from inclusion in cosmetic products, including cadmium, mercury and lead, as well as for the presence of microbiological contaminants such as *Staphylococcus aureus, Pseudomonas aeruginosa* and *Candida* yeast, in an accredited laboratory (via International Laboratory Accreditation Cooperation (ILAC) Mutual Recognition Agreement). The tests confirmed the absence of prohibited substances as wells as microbiological contamination.

Safety and toxicology is than evaluated by applying the formulation to human volunteers in a controlled study, in accordance with European Union standards.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of lightening skin in a subject in need thereof, the method comprising administering to the subject a therapeutically effective amount of a compound of the general Formula I:

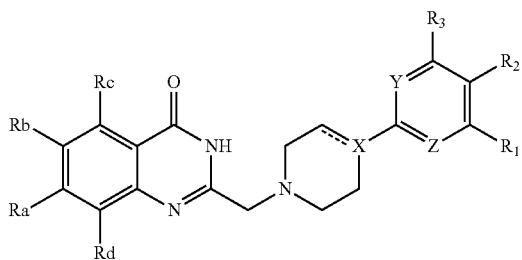

Formula I or a pharmaceutically acceptable salt thereof,
wherein:
the dashed line denotes a saturated or non-saturated bond;
X is selected from the group consisting of CH, C and N, such that when X is C the dashed line denotes a non-saturated bond and when X is CH or N the dashed line denotes a saturated bond;
Y is N or $CR_4$;
Z is N or $CR_5$; and
Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted,
thereby lightening the skin.

2. The method of claim 1, wherein at least one of $R_1$-$R_5$ is selected from the group consisting of hydroxy and a moiety having the general Formula II:

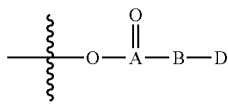

Formula II wherein:
A is selected from the group consisting of C and S=O;
B is absent or is a substituted or non-substituted, saturated or non-saturated alkylene chain; and
D is selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted.

3. The method of claim 2, wherein $R_1$ is selected from the group consisting of hydroxy and said moiety having the general Formula II.

4. The method of claim 2, wherein said A is a carbon atom.

5. The method of claim 1, wherein $R_2$-$R_5$ are each hydrogen.

6. The method of claim 1, wherein Ra-Rd are each hydrogen.

7. The method of claim 1, wherein said X is N.

8. The method of claim 1, wherein said Y is $CR_4$ and said Z is $CR_5$.

9. The method of claim 1, wherein said compound is 2-((4-(3-hydroxyphenyl)piperazin-1-yl)methyl)quinazolin-4-one:

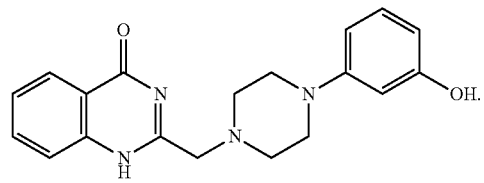 [SMILES: O=c1nc(CN2CCN(c3cccc(O)c3)CC2)[nH]c2ccccc12]

10. A method of treating uneven skin pigmentation in a subject in need thereof, the method comprising administering to the subject a therapeutically effective amount of a compound of the general Formula I:

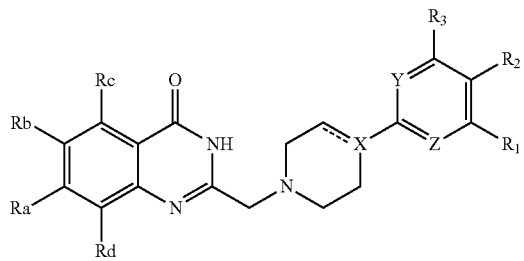

Formula I or a pharmaceutically acceptable salt thereof,
wherein:
the dashed line denotes a saturated or non-saturated bond;
X is selected from the group consisting of CH, C and N, such that when X is C the dashed line denotes a non-saturated bond and when X is CH or N the dashed line denotes a saturated bond;
Y is N or $CR_4$;
Z is N or $CR_5$; and
Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted, thereby treating the uneven skin pigmentation.

11. The method of claim 10, wherein at least one of $R_1$-$R_5$ is selected from the group consisting of hydroxy and a moiety having the general Formula II:

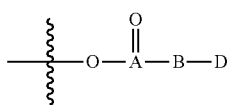

Formula II wherein:

A is selected from the group consisting of C and S=O;

B is absent or is a substituted or non-substituted, saturated or non-saturated alkylene chain; and D is selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted.

12. The method of claim 11, wherein $R_1$ is selected from the group consisting of hydroxy and said moiety having the general Formula II.

13. The method of claim 11, wherein said A is a carbon atom.

14. The method of claim 10, wherein $R_2$-$R_5$ are each hydrogen.

15. The method of claim 10, wherein Ra-Rd are each hydrogen.

16. The method of claim 10, wherein said X is N.

17. The method of claim 10, wherein said Y is $CR_4$ and said Z is $CR_5$.

18. The method of claim 10, wherein said compound is 2-((4-(3-hydroxyphenyl)piperazin-1-yl)methyl)quinazolin-4-one:

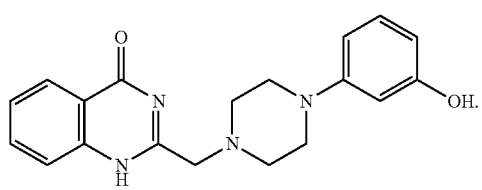 [SMILES: O=c1nc(CN2CCN(c3cccc(O)c3)CC2)[nH]c2ccccc12]

19. A method of improving the appearance of aging skin in a subject in need thereof, the method comprising administering to the subject a therapeutically effective amount of a compound of the general Formula I:

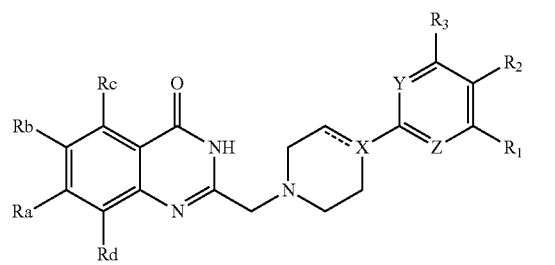

Formula I or a pharmaceutically acceptable salt thereof, wherein:

the dashed line denotes a saturated or non-saturated bond;

X is selected from the group consisting of CH, C and N, such that when X is C the dashed line denotes a non-saturated bond and when X is CH or N the dashed line denotes a saturated bond;

Y is N or $CR_4$;

Z is N or $CR_5$; and

Ra-Rd, and $R_1$-$R_5$ are each independently selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted, thereby improving the appearance of the aging skin.

20. The method of claim 19, wherein at least one of $R_1$-$R_5$ is selected from the group consisting of hydroxy and a moiety having the general Formula II:

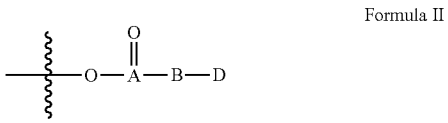

Formula II wherein:

A is selected from the group consisting of C and S=O;

B is absent or is a substituted or non-substituted, saturated or non-saturated alkylene chain; and D is selected from the group consisting of hydrogen, alkyl, alkenyl, alkynyl, cycloalkyl, heteroalicyclic, aryl, heteroaryl, hydroxy, alkoxy, aryloxy, thiohydroxy, thioalkoxy, thioaryloxy, halide, amine, amide, carbonyl, thiocarbonyl, carboxy, thiocarboxy, epoxide, sulfonate, sulfonyl, sulfinyl, sulfonamide, nitro, nitrile, isonitrile, thiirane, aziridine, nitroso, hydrazine, sulfate, azide, phosphonyl, phosphinyl, urea, thiourea, carbamyl and thiocarbamyl, each being substituted or non-substituted.

21. The method of claim 20, wherein $R_1$ is selected from the group consisting of hydroxy and said moiety having the general Formula II.

22. The method of claim 20, wherein said A is a carbon atom.

23. The method of claim 19, wherein $R_2$-$R_5$ are each hydrogen.

24. The method of claim 19, wherein said X is N.

25. The method of claim 19, wherein said Y is $CR_4$ and said Z is $CR_5$.

26. The method of claim 19, wherein said compound is 2-((4-(3-hydroxyphenyl)piperazin-1-yl)methyl)quinazolin-4-one:

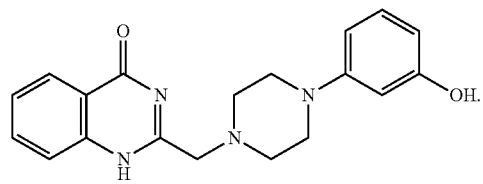 [SMILES: O=c1nc(CN2CCN(c3cccc(O)c3)CC2)[nH]c2ccccc12]

27. The method of claim 1, wherein said administering comprises topical administration.

28. The method of claim 27, wherein said compound forms a part of a pharmaceutical composition formulated for topical administration.

29. The method of claim 10, wherein said administering comprises topical administration.

30. The method of claim 19, wherein said administering comprises topical administration.

* * * * *